April 13, 1976 L. E. CARRIER Plant Pat. 3,865
CARNATION PLANT ENTITLED
LUCY CARRIER
Filed April 7, 1975
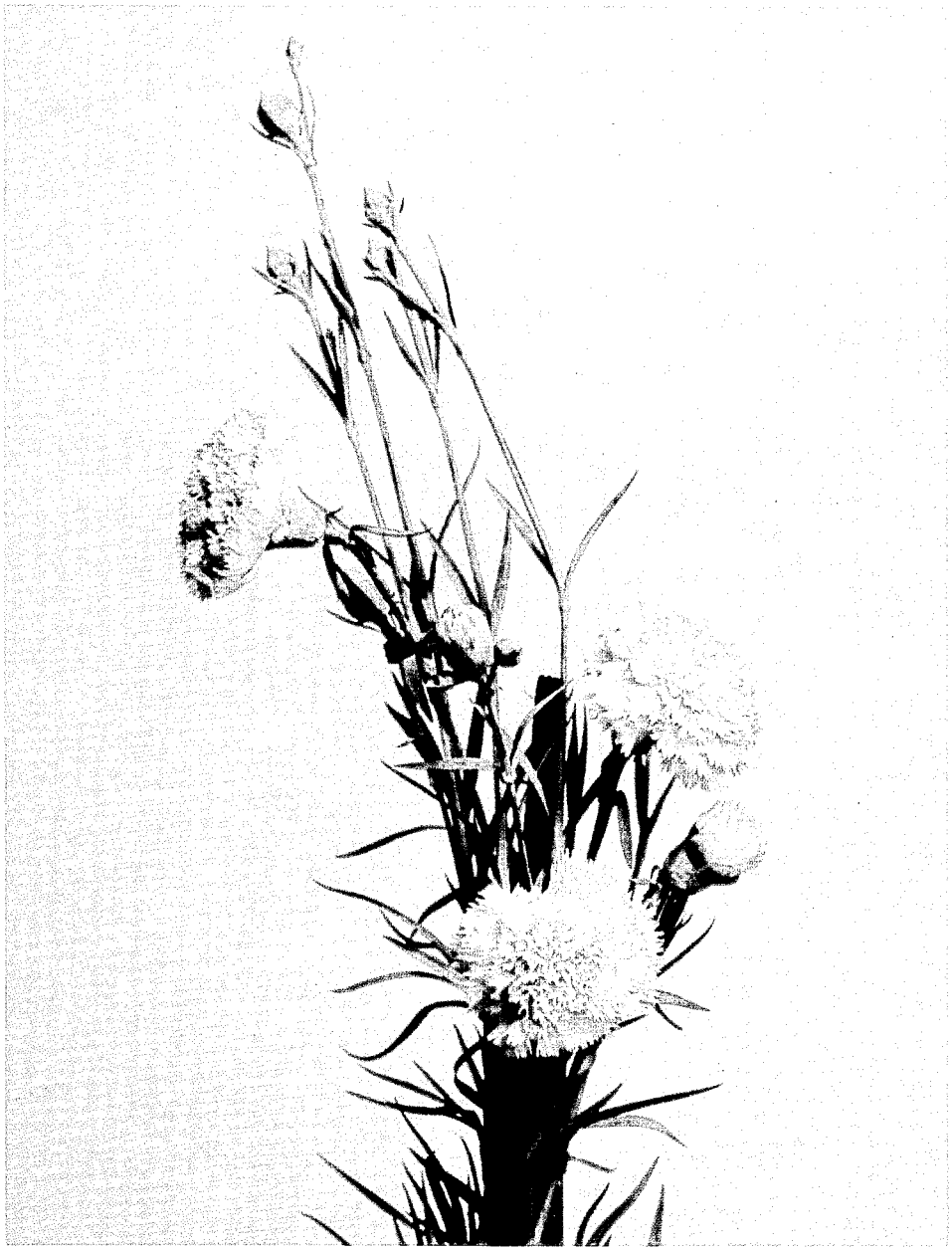

United States Patent

Plant Pat. 3,865

Patented Apr. 13, 1976

3,865

CARNATION PLANT ENTITLED LUCY CARRIER

Leonard E. Carrier, 1911 Sheridan Road, Encinitas, Calif. 92024

Filed Apr. 7, 1975, Ser. No. 565,622

Int. Cl. A01h *5/00*

U.S. Cl. Plt—71 1 Claim

The present invention relates to a new and distinct cultivar of carnation plant, Lucy Carrier, which was originated by me by crossing unnamed and unpatented seedlings.

SUMMARY OF DISCLOSURE

This invention relates to a new and distinct cultivar of carnation plant characterized particularly as to novelty by the unique combination of a very vigorous and free-breaking plant habit, with strong and straight stems; superior resistance to soil-borne diseases such as *Fusarium, oxysporium* and *roseum* and other root-rots such as damping off, water molds, and the like; large, serrated flowers which open fully without bursting the calyx and causing "splits"; a distinctive and attractive pink flower color which fades evenly and beautifully; a distinctive and pleasing delicate fragrance; and good heat tolerance which is superior to that of the parent lines and the so-called "Sim."

The primary objectives of this breeding were to produce an improved carnation cultivar having improved disease resistance and production qualities, along with improved flower color, size and form, as well as less tendency of the calyx to burst and cause "splits" as the flowers open fully, which is so typical of the species botanically known as *Dianthus caryophyllus*. These objectives were fully achieved, along with other desirable improvements, as evidenced by the following unique combination of principal characteristics which are outstanding in my new cultivar, Lucy Carrier, and which distinguish it from its parents, as well as from all other carnations of which I am aware:

1. A very vigorous and free-breaking plant habit with strong and straight stems;
2. Superior resistance to soil-borne diseases such as *Fusarium oxysporium* and *roseum* and other root-rots such as damping off, water molds, and the like;
3. Large, serrated flowers which open fully without bursting the calyx and causing "splits";
4. A distinctive and attractive pink flower color which fades evenly and beautifully;
5. A distinctive and pleasing fragrance.

Asexual reproduction of my new carnation variety by side shoot cuttings rooted in peat and "Perlite" under mist, as performed under my direction and control at Encinitas, Calif., shows that the foregoing characteristics and distinctions come true and are established and transmitted through succeeding propagations.

The accompanying drawing illustrates typical specimens of the vegetative growth and flowers of my new carnation in different stages of development and as depicted in color as nearly true as it is reasonably possible to make the same in a color illustration of this character.

The following is a detailed description of my new carnation cultivar, Lucy Carrier, with color terminology in accordance with Robert Ridgway's Color Standards and Nomenclature (1912 edition), except where general color terms of ordinary dictionary significance are obvious:

PLANT

Botanical classification: *Dianthus caryophyllus.*

Breeding: Seedling.

*Female parent.*—Cross between Corona (unpatented) and inbred numbered seedling.

*Male parent.*—Cross between two inbred numbered seedings of different origins.

Form: Erect, but free-branching.

Growth: Vigorous and rapid, many of nodes having buds from both sides, the upper six being flower buds, below that buds are vegetative frequently two to a node depending on the season and the light intensity.

Height: 80 to 100 cm.

Classification: Greenhouse type, suitable for cut flower production as a standard (one bloom per stem).

Propagation: Holds its distinguishing characteristics through succeeding propagations by rooted cuttings.

Locality where grown and observed: Encinitas, Calif.

Disease resistance: The new cultivar has shown no evidence of Fusariums or other root rots, as determined by extensive tests in highly infested soils inoculated with as many strains of fungi as are locally available in the area of Encinitas, Calif; tests conducted without chemical or steam sterilization of the soil.

Temperature tolerance: Not hardy to cold, but grows best at temperatures above 10° C.; has good resistance to hot weather in summer months of August and September at Encinitas, Calif., without hardening of growth and with only little reduction of flower size and little flower fading; no marked fading of outer flower petals even when bloom is past maturity.

Blooming period: Blooms under both long and short photoperiods.

BUD

Lobes of calyx overlap in tight bud and seldom split.

Length: About 3 cm.

Diameter: About 2½ cm.

Color: Leaf green, Plate XLI 29. When sepals first divide, color is Pale Amaranth Pink, Plate XII 67. When petals begin to unfurl, color is Pale Amaranth Pink, Plate XXII 67. When half blown, inside of petals color is Pale Amaranth Pink, Plate XXII 67; and reverse of petals color is Pale Amaranth Pink, Plate XXII 67.

PEDUNCLE

Strength: Strong.

Color: Leaf green, Plate XLI 29.

BLOOM

Size: Diameter is from 7 to 8 cm. Depth is from 5 to 6 cm.

Stem: Consists of 9 nodes. Length is from about 50 cm. to 60 cm. Diameter is from about 4 mm. to 5 mm. at base, and about 4 mm. at base of calyx. Color is green.

Form: Generally round, with high well developed crown, when fully open, calyx is completely hidden.

Petalage: From 60 to 85 petals. The outer petals are about 4½ cm. wide and about 5 cm. long. The center petals are about 3 cm. wide and about 5 cm. long.

Stigmas: About 2½ cm. long, white in color, usually 3 in number and protrude from the flower soon after buds turn color.

Color: Outer petals are Pale Amaranth Pink, Plate XXII 67. Base of petals are Pale Amaranth Pink, Plate XXII 67. Inside of petals are Pale Amaranth Pink, Plate XXII 67. Reverse of petals is Pale Amarnath Pink, Plate XXII 67.

General tonality: Soft even pink, somewhat decreasing in intensity from the center of the bloom and around the edges with age.

Petals: Texture is soft.

*Form.*—Each petal has 6 or more serrations per cm.; deep serrations 5 mm. alternating with shallower 2 mm. serrations; general outline of outer portions semicircular, and inner portions taper to 2 cm. to a 5 mm. stalk; when reflexed only the stalk is inside the calyx.

*Opening.*—Outer petals expand before the center petals. At this time stigmas appear. Calyx is exceptionally strong and no splitting has yet occurred.

*Fragrance.*—A delicate pleasant fragrance, only slightly spicy.

FOLIAGE

Form: From flat to nearly concave.

Size: About 5 to 10 mm. wide and from about 14 cm. to 15 cm. long.

Quantity: Two leaves per node, with nodes spaced about 10 cm. to 12 cm. apart.

Color:

*Young.*—Upper side: Leaf green, Plate XLI 29, Under side: Leaf green, Plate XLI 29.

*Mature.*—Upper side: Leaf green, Plate XLI 29. Under side: Leaf green, Plate XLI 29.

Texture: Smooth.

I claim:

1. A new and distinct cultivar of carnation plant, Lucy Carrier, substantially as herein shown and described, characterized particularly as to novelty by the unique combination of a very vigorous and free-breaking plant habit, with strong and straight stems, superior resistance to soil-borne diseases such as *Fusarium oxysporium* and *roseum* and other root-rots such as damping off, water molds, and the like, large, serrated flowers which open fully without bursting the calyx and causing "splits," a distinctive and attractive pink flower color which fades evenly and beautifully, a distinctive and pleasing delicate fragrance, and good heat tolerance which is superior to that of the parent lines and the so-called "Sim."

No references cited.

ROBERT E. BAGWILL, Primary Examiner